United States Patent [19]

Klimisch

[11] Patent Number: 5,021,405

[45] Date of Patent: Jun. 4, 1991

[54] EMOLLIENT DURABILITY ENHANCING SILOXANES

[75] Inventor: Helen M. Klimisch, Midland, Mich.

[73] Assignee: Dow Corning Corporation, Midland, Mich.

[21] Appl. No.: 488,163

[22] Filed: Mar. 5, 1990

[51] Int. Cl.$^5$ .......................................... A61K 31/695
[52] U.S. Cl. ...................................... 514/63; 514/762; 424/525
[58] Field of Search ................................. 514/63, 762

[56] References Cited

U.S. PATENT DOCUMENTS

| | | | |
|---|---|---|---|
| 3,818,105 | 6/1974 | Coopersmith et al. | 424/358 |
| 3,852,075 | 12/1974 | Basadur | 106/11 |
| 4,113,677 | 9/1978 | Svedas et al. | 260/23 |
| 4,246,285 | 1/1981 | Van Duzee | 424/358 |
| 4,271,215 | 6/1981 | Coon | 427/387 |
| 4,477,514 | 10/1984 | Gee et al. | 428/264 |
| 4,559,227 | 12/1985 | Chandra et al. | 424/70 |
| 4,563,347 | 1/1986 | Starch | 424/70 |
| 4,749,732 | 6/1988 | Kohl et al. | 524/43 |
| 4,810,253 | 3/1989 | Kasprzak et al. | 8/137 |
| 4,848,981 | 7/1989 | Kazprzak et al. | 8/137 |
| 4,857,212 | 8/1989 | Ona et al. | 252/8.6 |

*Primary Examiner*—Leonard Schenkman
*Attorney, Agent, or Firm*—Jim L. DeCesare

[57] ABSTRACT

A method of enhancing the durability of an emollient material on a substrate by forming a mixture of an emollient material and an effective amount of an organosilicon compound, and applying the mixture to the substrate to be treated. The organosilicon compound is either an aminofunctional, amidofunctional, or carboxyfunctional, polysiloxane. A skin conditioning composition of enhanced durability is also disclosed which is a mixture of an emollient material and an effective amount of an organosilicon compound which is either an aminofunctional, amidofunctional, or carboxy functional, polysiloxane.

18 Claims, No Drawings

EMOLLIENT DURABILITY ENHANCING SILOXANES

BACKGROUND OF THE INVENTION

This invention relates to the enhancement of the durability of emollient materials with certain organosilicon compounds. More particularly, the durability of mineral oil, for example, on human skin is enhanced by mixing the emollient with one of aminofunctional, amidofunctional, or carboxyfunctional, polysiloxanes.

Mineral oil is a highly refined, colorless, tasteless, and odorless, liquid mixture of hydrocarbons obtained from petroleum, that has been used medicinally as an internal lubricant and in the manufacture of various salves and ointments. It is also known as medicinal oil, white mineral oil, heavy mineral oil, light mineral oil, liquid paraffin, and paraffin oil. Mineral oil has long been the emollient of choice in creams and lotions. It is second only to water as a moisturizer ingredient. Mineral oil acts as a moisturizer primarily through the functioning of the ingredient as an occlusive barrier. The water content of the outer layers of the stratum corneum of the human skin is a controlling factor in the appearance of dry skin symptoms. When the stratum corneum contains an adequate amount of water within the range of ten to twenty percent, the skin remains flexible. However, when the water content falls below ten percent, the stratum corneum often becomes brittle and rough, and can exhibit scaling and cracking.

The stratum corneum receives its water from the deep layers of the epidermis by diffusion or when it is brought into direct contact with water. The diffusion process is controlled by the water content of the skin, as well as the concentration gradient. In a very dry environment, the water loss from the external skin layers can be significant and often exceeds the rate of replacement by diffusion. An occlusive barrier of mineral oil, for example, placed onto the surface of the skin acts to retard the water loss to the environment and allows the skin surface to rehydrate by the diffusion process. Due to the effectiveness, low cost, and safety, of petroleum derivatives such as mineral oil, it serves as a useful occlusive moisturizer and contributes to dry skin prevention by protection and moisture retention, as well as dry skin repair by emolliency, lubricity, and moisture restoration.

While mineral oil has been found to be an effective and economical emollient for skin care applications, and provides softening, smoothing, and a protective action on skin, it nevertheless suffers from the disadvantage that it is easily removed from the skin by washing the skin with soap. Thus, the effectiveness and long term benefits of mineral oil enumerated above are of a limited duration. However, in accordance with the present invention, it has been discovered that certain aminofunctional, amidofunctional, and carboxyfunctional, organosilicon compounds act as durability enhancers when mixed with mineral oil, and therefore provide skin care formulations that a consumer can perceive as being longer lasting and more aesthetically pleasing.

It is not new, as noted above, to employ mineral oil in skin conditioning formulations. For example, this feature is clearly taught, for example, in U.S. Pat. No. 3,818,105, issued June 18, 1974, and in U.S. Pat. No. 4,246,285, issued Jan. 20, 1981. Aminofunctional, amidofunctional, and carboxyfunctional, organosilicon compounds are also not new, and certain of such siloxanes are shown, for example, in U.S. Pat. No. 4,271,215, issued June 2, 1981; U.S. Pat. No. 4,477,514, issued Oct. 16, 1984; U.S. Pat. No. 4,559,227, issued Dec. 17, 1985; U.S. Pat. No. 4,563,347, issued Jan. 7, 1986; U.S. Pat. No. 4,749,732, issued June 7, 1988; U.S. Pat. No. 4,810,253, issued Mar. 7, 1989; U.S. Pat. No. 4,848,981, issued July 18, 1989; and in U.S. Pat. No. 4,857,212, issued Aug. 15, 1989. However, none of these references teach the combination of mineral oil with such siloxanes and there use on the skin as durability enhancers. Formulations containing mineral oil and an aminofunctional siloxane are know as exemplified by U.S. Pat. No. 3,852,075, issued Dec. 3, 1974, and U.S. Pat. No. 4,113,677, issued Sept. 12, 1978, but such formulations are employed to clean and polish automotive vehicles rather than as personal skin care applications.

SUMMARY OF THE INVENTION

This invention relates to a method of enhancing the durability of an emollient material on a substrate by forming a mixture of an emollient material and an effective amount of an organosilicon compound, and applying the mixture to the substrate to be treated. The organosilicon compound is either an aminofunctional, amidofunctional, or carboxyfunctional, polysiloxane.

Preferred embodiments of the present invention include an aminofunctional polysiloxane having the formula $Me_3SiO(Me_2SiO)_x(MeRSiO)_ySiMe_3$ in which Me is methyl; R is the functional group $-(C_4H_8)NH(CH_2)_2NH_2$; x is an integer from fifty to one thousand; and y is an integer from one to fifty preferably one to twenty. The amidofunctional polysiloxane preferably has the formula $Me_3SiO(Me_2SiO)_x(MeRSiO)_ySiMe_3$ in which Me is methyl; R is the functional group $-(C_4H_8)NH(CH_2)_2NHCOCH_3$; x is an integer from fifty to one thousand preferably fifty to one hundred; and y is an integer from one to fifty preferably one to ten. Preferably, the carboxyfunctional polysiloxane compound has the formula $Me_3SiO(Me_2SiO)_x(MeRSiO)_ySiMe_3$ in which Me is methyl; R is the functional group $-(C_3H_6)COOH$; x is an integer from fifty to one thousand preferably one hundred to three hundred; and y is an integer from one to fifty.

The emollient and the polysiloxane may be present in the mixture in the ratio of four to one, more preferably two to one. The mixture of the emollient and the polysiloxane may, if desired, include a volatile cyclic siloxane solvent, and the solvent can be a low viscosity polydimethylcyclosiloxane fluid, for example, which is a mixture of cyclic tetramers and pentamers and having a viscosity of about 2.5 centistokes measured at twenty-five degrees Centigrade. The mixture should contain about five to ten percent by weight of the emollient and the polysiloxane in the volatile cyclic siloxane solvent. The emollient may be a material such as mineral oil, mink oil, lanolin oil, and petrolatum.

The invention also relates to a skin conditioning composition of enhanced durability which is a mixture of an emollient material and an effective amount of an organosilicon compound. The organosilicon compound, as noted above, is either an aminofunctional, amidofunctional, or carboxyfunctional, polysiloxane.

These and other features, objects, and advantages, of the herein described present invention will become more apparent from a consideration of the following detailed description thereof.

DETAILED DESCRIPTION OF THE INVENTION

In accordance with the present invention, there is provided a concept which relates to the enhancement of the durability of emollient materials with certain organosilicon compounds. The durability on human skin is enhanced by mixing an emollient with either one of an aminofunctional, amidofunctional or carboxyfunctional, polysiloxanes. These aminofunctional amidofunctional, and carboxyfunctional, organosilicon compounds are well known in the prior art, and such compounds as well as methods for preparing these compounds can be found in U.S. Pat. No. 4,477,514, issued Oct. 16, 1984, which shows carboxyfunctional siloxanes; U.S. Pat. No. 4,559,227, issued Dec. 17, 1985, which shows aminofunctional siloxanes; and U.S. Pat. No. 4,848,981, issued July 18, 1989, which shows the amidofunctional siloxanes, of the present invention. In the interest of providing a full and complete disclosure of the present invention, these patents are considered incorporated herein by reference. However, a brief description of these functional siloxanes is set forth hereinbelow.

The amine functional siloxane polymer has the formula $$R_{3-z'}Q_zSiO[R_2'SiO]_x[R'QSiO]_ySiQ_zR_{3-z'}$$

wherein R' denotes an alkyl group of 1 to 4 carbons or a phenyl group, with the proviso that at least 50 percent of the total R' groups are methyl; Q denotes an amine functional substituent of the formula —R"Z, wherein R" is a divalent alkylene radical of 3 to 6 carbon atoms or a radical of the formulation —CH$_2$CH$_2$CH$_2$OCH$_2$—CHOHCH$_2$— and Z is a monovalent radical selected from the group consisting of NR$_2$''', NR'''(CH$_2$)$_n$NR$_2$'''; and $$\begin{array}{c} O \\ \| \\ NR'''(CH_2)_nN(R''')CR'''' \end{array}$$

wherein R''' denotes hydrogen or an alkyl group of 1 to 4 carbons, R'''' denotes an alkyl group of 1 to 4 carbons and n is a positive integer from 2 to 6; z has a value of 0 or 1; x has an average value of 25 to 3000; y has an average value of 0 to 100 when z is 1, and y has an average value of 1 to 100 when z is 0.

The amidofunctional polysiloxane is a triorganosiloxane-endblocked polydiorganosiloxane having an average of 50 to 1000 siloxane units per molecule with an average of 1 to 50 of the siloxane unites per molecule being amide-containing siloxane units. The amide-containing siloxane units bear a substituent of the formula $$\begin{array}{c} -R'(NCH_2CH_2)_nNR'' \\ |\quad\quad\quad\quad | \\ X'\quad\quad\quad\quad X \end{array}$$

wherein n is 0 or 1, R' denotes an alkylene radical of 3 to 6 carbon atoms, and R" denotes a hydrogen radical or an alkyl radical of 1 to 6 carbon atoms, X denotes an acyl radical of the formula $$\begin{array}{c} O \\ \| \\ -CR''' \end{array},$$

X' denotes a hydrogen radical or X, and R''' denotes an alkyl radical of 1 to 4 carbon atoms and substantially all other organic substituents in the polydiorganosiloxane being methyl groups.

The amidofunctional silicone component in accordance with this invention consists essentially of a triorganosiloxane-endblocked polydiorganosiloxane which contains amidoalkyl substituents. Triorganosiloxane-endblocked polydiorganosiloxanes (amidofunctional silicone) consist essentially of terminal triorganosiloxane units of the formula R$_3$SiO$_{\frac{1}{2}}$ and backbone diorganosiloxane units of the formula R$_2$SiO$_{2/2}$. Trace amounts of other siloxane units in amidofunctional silicone, such as SiO$_{4/2}$ and RSiO$_{3/2}$, which are normally present as impurities in commercial polydiorganosiloxanes may be present. Preferably there are no SiO$_{4/2}$ units or RSiO$_{3/2}$ units in the amidofunctional silicones.

The R radicals of the above siloxane units are substantially either amide-containing radicals of the formula $$\begin{array}{c} -R'(NCH_2CH_2)_nNR'' \\ |\quad\quad\quad\quad | \\ X'\quad\quad\quad\quad X \end{array}$$

or methyl radicals. Minor amounts of other organic substituents which are normally present as impurities in commercial polydiorganosiloxanes may be present. It should be understood, for example, that the amidofunctional silicones of this invention are often prepared by acylation of corresponding aminofunctional silicones. Consequently, the amidofunctional silicones may also contain residual aminofunctional siloxane units. For example, siloxane unites such as H$_2$NCH$_2$CH$_2$NHCH$_2$CH(CH$_3$)CH$_2$SiO$_{2/2}$ or H$_2$NCH$_2$CH$_2$CH$_2$SiO$_{2/2}$ may also be present in the amidofunctional silicones useful in this invention. However, for the purposes of this invention it is preferred to employ silicone oils that do not contain significant levels (more than 25 percent of the number of amidofunctional substituents) of the unmodified aminofunctional siloxane units.

In the formula for the amide-containing radicals, R' denotes an alkylene radical of 3 to 6 carbon atoms, such as —CH$_2$CH$_2$CH$_2$—, —CH$_2$CH$_2$CH$_2$CH$_2$—, —CH$_2$CH(CH$_3$)CH$_2$—, —CH$_2$CH$_2$CH$_2$CH$_2$CH$_2$—, and —CH$_2$CH(CH$_2$CH$_3$)CH$_2$—. Amidofunctional silicones wherein the silicon bonded, amide-containing radicals have a trimethylene radical or an alkylated trimethylene radical, such as —CH$_2$CH(CH$_3$)CH$_2$—, as the R' radical are preferred because of ease of synthesis and availability.

R" denotes a hydrogen radical, which is a preferred R" radical, or an alkyl radical of 1 to 6 carbon atoms, such as methyl, ethyl, propyl, butyl, and isobutyl.

In the formula for the amide-containing radicals, n has a value of 0 or 1, so that the radical may contain one or two nitrogen atoms. X denotes an acyl radical of the formula $$\begin{array}{c} O \\ \| \\ -CR''' \end{array}$$

and X' denotes a hydrogen radical or X. In the acyl radical, R''' denotes an alkyl radical of 1 to 4 carbon atoms such as methyl, ethyl, propyl, isopropyl, or butyl.

In accordance with the above, triorganosiloxane-endblocked polydiorganosiloxanes preferred for use in the method of this invention consists essentially of siloxane units selected from the following:

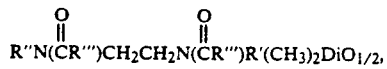

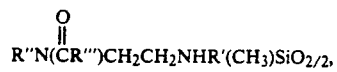

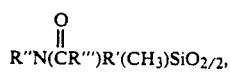

$(CH_3)_3SiO_{\frac{1}{2}}$, and $(CH_3)_2SiO_{2/2}$ where R', R", and R''' have the same meanings as described above. It should be understood that any of the siloxane units having non-acylated nitrogen atoms can also be present in their salt form. It is well known that the salt form occurs when such polymers are neutralized by acids such as mineral acids or carboxylic acids.

The silicone polymers of this invention may contain amide-containing siloxane units of the formula

wherein R', R", and R''' have the same meanings as described above. These amide-containing units have a ratio of acyl groups to nitrogen atoms of about 0.5.

The carboxyfunctional silicones of the invention have the formula

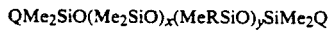

wherein Me is a methyl radical, R is a carboxyfunctional radical, said carboxyfunctional radical being selected from the group consisting of carboxyalkyl radicals and carboxythioalkyl radicals, Q is selected from the group consisting of R, Me and OH groups, x has a value of 1 to 1000, and y has a value of 1 to 100.

As referred to herein, a carboxyfunctional radical is a monovalent radical which contains the —COOH radical, and is attached to a silicon atom of the main molecular chain by a divalent linking group. Direct attachment to the silicon atom is through a silicon to carbon bond.

Divalent linking groups contemplated for use in the present invention are either alkylene groups containing from 2 to 9 carbon atoms, or thioalkylene groups, containing 2 to 8 carbon atoms and one sulfur atom present as a thioether group.

Those carboxyfunctional radicals wherein the divalent linking group is an alkylene group are referred to herein as carboxyalkyl radicals; those carboxyfunctional radicals wherein the divalent linking group is a thioalkylene group are referred to herein as carboxythioalkyl radicals.

Specific examples of carboxyalkyl radicals include, but are not limited to —CH$_2$CH$_2$COOH, —CH$_2$CH(CH$_3$)COOH, —CH$_2$CH(C$_2$H$_5$)CH$_2$COOH, —CH$_2$CH(CH$_3$)CH(CH$_3$)CH$_2$COOH, and the like. The —CH$_2$CH(CH$_3$) COOH radical is a preferred carboxyalkyl radical for the practice of the present invention.

Specific examples of carboxythioalkyl radicals include, but are not limited to —CH$_2$CH$_2$SCOOH, —(CH$_2$)$_3$SCOOH, —CH$_2$CH(CH$_3$)SCH$_2$COOH, —CH$_2$CH$_2$SCH$_2$COOH, —CH$_2$CH(C$_2$H$_5$)SCH$_2$COOH, and the like. The —CH$_2$CH$_2$SCH$_2$COOH radical is a preferred carboxythioalkyl radical for the practice of the present invention.

Examples of emollients and moisturizers which may be used in this invention include straight, branched or cyclic hydroxy compounds such as alcohols containing 1 to 30 carbon atoms; straight, branched, or cyclic carboxylic acids containing 1 to 31 carbon atoms; acid esters containing C$_1$ to C$_{30}$ carboxylic acids esterfied with C$_1$ to C$_{30}$ alcohols; alcohol ethers containing 1 to 30 carbon atoms; alkanes of the formula H—(CH$_2$)$_n$—H, wherein n is 5 to 30; and siloxanes. Examples of such functional materials include 2-ethylhexyl oxystearate; arachidyl propionate; 2-ethylhexyl adipate; isopropyl myristate; ethanol; stearyl alcohol; propylene glycol; propionic acid; stearic acid; polyoxypropylene cetyl alcohol; polyoxypropylene lanolin alcohol; Carbowax® 300; petroleum jelly; mineral oil; aliphatic hydrocarbons such as mineral spirits; lanolin and lanolin derivatives such a acetylated lanolin and isopropyl lanolate; hexamethyldisiloxane; cyclic polydimethylsiloxane; linear polydimethylsiloxane; polypheylmethylsiloxane; and poly dimethyl/trimethylsiloxane. Other phenyl, ethyl and vinyl substituted polysilanes may also be included in the products of this invention.

In order to illustrate the durability enhancement of the siloxanes of the present invention, durability enhancement data was collected for a variety of emollients. A soap washing test procedure was used in order to measure the influence of the silicones on the durability of the various emollients. The emollients considered were mineral oil, mink oil lanolin oil, and petrolatum. The test procedure was used to measure silicone substantivity on human skin. Specifically, the method was based on Attenuated Total Reflectance/Fourier Transform Infrared Spectrophotometric (ATR/FTIR) analysis, in which prism skin studies were conducted and analyzed based on the reflection of energy at the interface. Instrumentation included a NICOLET Model 20DX FTIR system, and a HARRICK Scientific Skin Analyzer. The ATR studies involved contact of the skin sample and prism. A hydration procedure was employed in order to increase the softness and flexibility of the skin surface which resulted in a less variable contact between the skin and prism. This hydration procedure included placing a water soaked towel against the skin test site for one minute prior to actual spectra collection. A skin test site selected was an area of about eighty square centimeters, and about ten to twelve milligrams of each solution tested was applied to the skin test site area in the form of a thin film using a small paint brush. From the data collected, it was possible to calculate percentages of ingredients remaining on the skin following various soap wash sequences. The soap employed was a 0.5 weight percent solution of IVORY bar soap, and a soap rub is defined as two passes over the test area with the soap solution cupped in the palm of the hand. One soap wash procedure included fifteen soap rubs and ten rinse rubs under cool running tap water. The test site was the volar forearm. The test solutions were applied to the skin test site on the forearm in the form of a mixture of the various silicones and emollients, dissolved in a volatile silicone fluid of low viscosity, such as polydimethylcyclosiloxane which is a mixture of tetramer and pentamer having a viscosity of about 2.5 centistokes measured at twenty-five degrees Centigrade. The solution contained five to ten percent by weight of the mixture in the solvent. The solvent was allowed to evaporate from the volar forearm region for fifteen to thirty minutes prior to the institution of the measurement procedures. The site was hydrated as noted above and initial spectrum was collected. The data included tests conducted with and without the presence of the various silicones in the test mixture, and at least two test runs were conducted for each mixture.

A simplified test procedure is illustrated as follows. A test area on the forearm was marked, and the test area was washed with the soap solution using fifteen rubs, followed by rinsing with ten rubs under cool running water. Excess moisture was blotted from the forearm with a towel. After one minute, the skin was hydrated for one minute using a towel saturated with water which was held loosely over the test area. Excess moisture was blotted, and at the end of thirty seconds a background scan was run. The test mixture was applied to the skin test area and the solvent allowed to evaporate. The skin was again hydrated for one minute and excess moisture was blotted off. After thirty seconds, a scan was run of the test area which represented an Initial using fifteen rubs followed by ten rinses, and the excess moisture was blotted off. After one minute, the skin was hydrated for one minute, blotted, and at the end of thirty seconds, a scan was run of the test area which represented a First Soap Wash Condition. Similar steps were repeated for second, third, and fourth, soap wash conditions. Baselines for infrared bands were defined and band heights were measured. The percent ingredient remaining on the skin was calculated using this data.

The following tables set forth the results of the foregoing procedures, and illustrate the concept of the present invention of enhancing the durability of various emollients with certain functional silicones. The tables indicate that the functional silicones enhance emollient durability and therefore provide a viable solution to dry, chapped, and rough skin, which results when the emollients are removed by washing. The siloxanes are soap wash resistant and have shown minimal or no dermal irritation The carboxyfunctional siloxane is known to possess the least dermal irritation of the siloxane types tested. The functional silicones used in the tables conform to the formula $Me_3SiO(Me_2SiO)_x(MeRSiO)_ySiMe_3$ in which Me is methyl and R is the functional group. Specifics of the R group and values of the integers x and y are set forth in the tables where appropriate. Unless otherwise indicated, the mixtures of emollient and silicone were in a ratio of four to one, and the mixtures were delivered in form of mixtures including a volatile cyclic siloxane. The compositions of the present invention may contain other adjuvants such as perfumes, fragrances, and preservatives, provided the addition of the adjuvant to the composition would not materially affect the basic and novel characteristics of the composition and would not materially change its fundamental characteristics.

TABLE I

EMOLLIENTS - NO SILICONE PERCENT REMAINING

| Test Condition | Mink Oil | Lanolin Oil | Mineral Oil | Petrolatum |
|---|---|---|---|---|
| Initial | 100 | 100 | 100 | 100 |
| 1st wash | 32 | 33 | 32 | 44 |
| 2nd wash | 19 | 21 | 16 | 34 |
| 3rd wash | 14 | 15 | 6 | 19 |
| 4th wash | — | — | 4 | 16 |
| 5th wash | — | — | 2 | 13 |

TABLE II

COMPOUNDS USED AMINE AND AMIDE FUNCTIONAL SILICONES

| Silicone | R-Group | M % R | x | y | x/y |
|---|---|---|---|---|---|
| A | $iBuNH(CH_2)_2NH_2$ | 1 | 97 | 1 | 91/1 |
| B | $iBuNH(CH_2)_2NH_2$ | 2 | 96 | 2 | 48/1 |
| C | $iBuNH(CH_2)_2NH_2$ | 5 | 188 | 10 | 19/1 |
| D | $iBuNH(CH_2)_2NH_2$ | 0.7 | 296 | 2 | 148/1 |
| E | $iBuNH(CH_2)_2NH_2$ | 0.5 | 445.8 | 2.2 | 203/1 |
| F | $iBuNH(CH_2)_2NH_2$ | 1.7 | 440.4 | 7.6 | 58/1 |
| G | $iBuNH(CH_2)_2NH_2$ | 0.25 | 796 | 2 | 398/1 |
| H | $iBuNH(CH_2)_2NHCOCH_3$ | 2 | 96 | 2 | 48/1 |

TABLE III

PERCENT REMAINING MINERAL OIL AND SILICONES

| Test Condition | SILICONES | | | | | | | |
|---|---|---|---|---|---|---|---|---|
| | H | A | B | C | D | E | F | G |
| INITIAL | 100 | 100 | 100 | 100 | 100 | 100 | 100 | 100 |
| 1st wash | 46 | 56 | 53 | 47 | 46 | 46 | 50 | 52 |
| 2nd wash | 28 | 38 | 35 | 35 | 40 | 32 | 34 | 41 |
| 3rd wash | 22 | 32 | 28 | 30 | 32 | 32 | 28 | 32 |
| 4th wash | 20 | 30 | 24 | 27 | 26 | 26 | 21 | 30 |
| 5th wash | 17 | 25 | 20 | 24 | 22 | 25 | 20 | 19 |

TABLE IV

PERCENT REMAINING MINERAL OIL AND SILICONES

| Test Condition | Polydimethylsiloxane (1) | | | H | Average A-G |
|---|---|---|---|---|---|
| | 100 DP | 550 DP | 6800 DP | | |
| INITIAL | 100 | 100 | 100 | 100 | 100 |
| 1st wash | 35 | 35 | 45 | 46 | 50 |
| 2nd wash | 24 | 20 | 37 | 28 | 36 |
| 3rd wash | 20 | 18 | 31 | 22 | 31 |
| 4th wash | 18 | 16 | 27 | 20 | 26 |
| 5th wash | 14 | — | 24 | 17 | 22 |

(1): 100 DP is 350 Centistoke fluid.
550 DP is hydroxy endblocked fluid with partial trimethyl capping.
6800 DP is a siloxane gum.

TABLE V

| | | % Mineral Oil Remaining | | | | | |
|---|---|---|---|---|---|---|---|
| Sample Number | Polymer Description | Initial Condition | 1st Wash | 2nd Wash | 3rd Wash | 4th Wash | 5th Wash |
| 1 | No Silicone | 100 | 32 | 16 | 6 | 4 | 2 |
| 2 | H | 100 | 56 | 34 | 25 | 20 | 14 |
| 3 | A | 100 | 40 | 26 | 18 | 16 | 14 |

TABLE V-continued

| Sample Number | Polymer Description | % Mineral Oil Remaining | | | | | |
|---|---|---|---|---|---|---|---|
| | | Initial Condition | 1st Wash | 2nd Wash | 3rd Wash | 4th Wash | 5th Wash |
| 4 | B | 100 | 52 | 27 | 18 | 19 | 13 |
| 5 | C | 100 | 40 | 28 | 25 | 18 | 14 |
| 6 | D | 100 | 58 | 36 | 30 | 17 | 8 |
| 7 | E | 100 | 66 | 41 | 34 | 26 | 24 |
| 8 | F | 100 | 58 | 37 | 28 | 17 | 15 |
| 9 | G | 100 | 33 | 30 | 18 | 20 | 5 |

TABLE VI

| | Compounds Used Carboxyfunctional Silicones | | | | |
|---|---|---|---|---|---|
| Reference | R-Group | M % R | x | y | x/y |
| J | iPr COOH | 3 | 201.7 | 6.3 | 32/1 |
| K | iPr COOH | 0.7 | 296 | 2 | 148/1 |
| L | iPr COOH | 3.3 | 288 | 10 | 29/1 |
| M | iPr COOH | 15 | 253 | 45 | 6/1 |

TABLE VII

| | Percent Remaining Mineral Oil and Silicone | | |
|---|---|---|---|
| Test Condition | J | K | L |
| INITIAL | 100 | 100 | 100 |
| 1st Wash | 44 | 42 | 29 |
| 2nd Wash | 30 | 33 | 19 |
| 3rd Wash | 24 | 28 | 14 |
| 4th Wash | 21 | 26 | 13 |
| 5th Wash | 19 | 22 | 15 |

TABLE VIII

| | Mineral Oil and Silicone Percent Silicone Remaining | | | | | |
|---|---|---|---|---|---|---|
| | Polydimethylsiloxane | | | | A-G | J-K |
| Test Condition | 100 DP | 550 DP | 6800 DP | H | Amino Avg. | Carboxylic Acid Avg. |
| INITIAL | 100 | 100 | 100 | 100 | 100 | 100 |
| 1st Wash | 35 | 35 | 45 | 46 | 50 | 43 |
| 2nd Wash | 24 | 20 | 37 | 28 | 36 | 32 |
| 3rd Wash | 20 | 18 | 31 | 22 | 31 | 26 |
| 4th Wash | 18 | 16 | 27 | 20 | 26 | 24 |
| 5th Wash | 14 | — | 24 | 17 | 22 | 20 |

TABLE IX

| | Mineral Oil and Silicone % Mineral Oil Remaining | | | |
|---|---|---|---|---|
| Test Condition | No Sil. | J | K | L |
| INITIAL | 100 | 100 | 100 | 100 |
| 1st Wash | 32 | 47 | 52 | 32 |
| 2nd Wash | 16 | 30 | 36 | 20 |
| 3rd Wash | 6 | 19 | 24 | 13 |
| 4th Wash | 4 | 13 | 22 | 6 |
| 5th Wash | 2 | 8 | 12 | 4 |

TABLE X

| | Two to One Mink Oil and Silicone % Mink Oil Remaining | | | |
|---|---|---|---|---|
| | No | Carboxylic Acid | | |
| Test Condition | Sil. | J | K | L |
| INITIAL | 100 | 100 | 100 | 100 |
| 1st Wash | 32 | 46 | 45 | 30 |
| 2nd Wash | 19 | 28 | 28 | 17 |
| 3rd Wash | 14 | 26 | 25 | 10 |

The mixture of emollient and silicone can be delivered to the skin in the form of emulsions, microemulsions, solutions, dispersions, lotions, gels, aerosols, solid sticks, ointments, and creams.

It will be apparent from the foregoing that many other variations and modifications may be made in the compounds, compositions, structures, and methods, described herein, without departing substantially from the essential features and concepts of the present invention. Accordingly, it should be clearly understood that the forms of the invention described herein are exemplary only and are not intended as limitations on the scope of the present invention as defined in the appended claims.

That which is claimed is:

1. A method of enhancing the durability of an emollient material on human skin comprising applying to human skin a mixture of an emollient material and an effective amount of an organosilicon compound, the organosilicon compound being an amidofunctional siloxane having an average of 50 to 1000 siloxane units per molecule with an average of 1 to 50 of the siloxane units per molecule being amide-containing siloxane units bearing a substituent of the formula

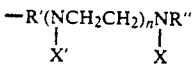

wherein n is 0 or 1, R' denotes an alkylene radical of 3 to 6 carbon atoms, and R" denotes a hydrogen radical or an alkyl radical of 1 to 6 carbon atoms, X denotes an acyl radical of the formula

X' denotes a hydrogen radical or X, and R''' denotes an alkyl radical of 1 to 4 carbon atoms and substantially all other organic substituents in the polysiloxane being methyl groups, the emollient material being selected from the group consisting of (i) straight, branched, and cyclic hydroxy compounds containing 1 to 30 carbon atoms, (ii) straight, branched, and cyclic carboxylic acids containing 1 to 31 carbon atoms, (iii) alkanes of the formula H—(CH$_2$)$_n$—H wherein n is 5 to 30, and (iv) siloxanes.

2. The method of claim 1 in which the amidofunctional polysiloxane is a compound having the formula Me$_3$SiO(Me$_2$SiO)$_x$(MeRSiO)$_y$SiMe$_3$ in which Me is methyl; R is the functional group —(C$_4$H$_8$)NH(CH$_2$)$_2$NHCOCH$_3$; x is an integer from fifty to one thousand; and y is an integer from one to fifty.

3. The method of claim 2 in which the emollient and the polysiloxane are present in the mixture in the ratio of four to one.

4. The method of claim 2 in which the emollient and the polysiloxane are present in the mixture in the ratio of two to one.

5. The method of claim 3 in which the mixture of the emollient and the polysiloxane includes a volatile cyclic siloxane solvent.

6. The method of claim 5 in which the volatile cyclic siloxane is a low viscosity polydimethylcyclosiloxane fluid.

7. The method of claim 6 in which the polydimethylcyclosiloxane fluid is a mixture of cyclic tetramers and pentamers and has a viscosity of about 2.5 centistokes measured at twenty-five degrees Centigrade.

8. The method of claim 7 in which the mixture contains about five to ten percent by weight of the emollient and the polysiloxane in the volatile cyclic siloxane solvent.

9. The method of claim 1 in which the emollient is a material selected from the group consisting of mineral oil, mink oil, lanolin oil, and petrolatum.

10. A skin conditioning composition of enhanced durability comprising a mixture of an emollient and an effective amount of an organosilicon compound, the organosilicon compound being an amidofunctional polysiloxane having an average of 50 to 1000 siloxane units per molecule with an average of 1 to 50 of the siloxane units per molecule being amide-containing siloxane units bearing a substituent of the formula

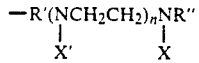

wherein n is 0 or 1, R' denotes an alkylene radical of 3 to 6 carbon atoms, and R'' denotes a hydrogen radical or an alkyl radical of 1 to 6 carbon atoms, X denotes an acyl radical of the formula

X' denotes a hydrogen radical or X, and R''' denotes an alkyl radical of 1 to 4 carbon atoms and substantially all other organic substituents in the polysiloxane being methyl groups, the emollient material being selected from the group consisting of (i) straight, branched, and cyclic hydroxy compounds containing 1 to 30 carbon atoms, (ii) straight, branched, and cyclic carboxylic acids containing 1 to 31 carbon atoms, (iii) alkanes of the formula $H-(CH_2)_n-H$ wherein n is 5 to 30, and (iv) siloxanes.

11. The composition of claim 10 in which the amidofunctional polysiloxane is a compound having the formula $Me_3SiO(Me_2SiO)_x(MeRSiO)_ySiMe_3$ in which Me is methyl; R is the functional group $-(C_4H_8)NH(CH_2)_2$; x is an integer from fifty to one thousand; and y is an integer from one to fifty.

12. The composition of claim 11 in which the emollient and the polysiloxane are present in the mixture in the ratio of four to one.

13. The composition of claim 11 in which the emollient and the polysiloxane are present in the mixture in the ratio of two to one.

14. The composition of claim 12 in which the mixture of the emollient and the polysiloxane includes a volatile cyclic siloxane solvent.

15. The composition of claim 14 in which the volatile cyclic siloxane is a low viscosity polydimethylcyclosiloxane fluid.

16. The composition of claim 15 in which the polydimethylcyclosiloxane fluid is a mixture of cyclic tetramers and pentamers and has a viscosity of about 2.5 centistokes measured at twenty-five degrees Centigrade.

17. The composition of claim 16 in which the mixture contains about five to ten percent by weight of the emollient and the polysiloxane in the volatile cyclic siloxane solvent.

18. The composition of claim 10 in which the emollient is a material selected from the group consisting of mineral oil, mink oil, lanolin oil, and petrolatum.

* * * * *